(12) United States Patent
Eckert et al.

(10) Patent No.: US 7,368,524 B2
(45) Date of Patent: May 6, 2008

(54) CATIONICALLY CURING TWO COMPONENT MATERIALS CONTAINING A NOBLE METAL CATALYST

(75) Inventors: Adrian S. Eckert, Munich (DE); Uwe H. Hoheisel, Tuerkenfeld (DE); Reinhold Hecht, Kaufering (DE)

(73) Assignee: 3M Innovative Properties Company, St. Paul, MN (US)

( * ) Notice: Subject to any disclaimer, the term of this patent is extended or adjusted under 35 U.S.C. 154(b) by 114 days.

(21) Appl. No.: 11/109,573

(22) Filed: Apr. 19, 2005

(65) Prior Publication Data

US 2006/0116445 A1 Jun. 1, 2006

(30) Foreign Application Priority Data

Apr. 30, 2004 (EP) ................................. 04010330

(51) Int. Cl.
C08G 65/04 (2006.01)
(52) U.S. Cl. ...................... 528/412; 523/109; 523/115; 528/91; 528/92; 528/416
(58) Field of Classification Search ...................... None
See application file for complete search history.

(56) References Cited

U.S. PATENT DOCUMENTS

| | | | |
|---|---|---|---|
| 2,716,123 A | 8/1955 | Frostick, Jr. et al. | |
| 2,750,395 A | 6/1956 | Phillips et al. | |
| 2,863,881 A | 12/1958 | Phillips et al. | |
| 2,985,667 A | 5/1961 | Tinsley et al. | |
| 3,018,262 A | 1/1962 | Schroeder | |
| 3,117,099 A | 1/1964 | Proops et al. | |
| 3,187,018 A | 6/1965 | Tinsley et al. | |
| 3,197,432 A | 7/1965 | Lamoreaux | |
| 3,220,972 A * | 11/1965 | Lamoreaux | 528/15 |
| 3,715,334 A | 2/1973 | Karstedt | |
| 3,775,352 A | 11/1973 | Leonard, Jr. | |
| 3,775,452 A * | 11/1973 | Karstedt | 556/10 |
| 3,814,730 A | 6/1974 | Karstedt | |
| 4,225,961 A | 9/1980 | Raggenbass | |
| 4,238,587 A | 12/1980 | Crivello | |
| 4,239,725 A | 12/1980 | Crivello | |
| 4,246,703 A | 1/1981 | Robinet | |
| 4,314,917 A | 2/1982 | Wolfrey | |
| 4,342,673 A | 8/1982 | Wolfrey | |
| 5,037,861 A * | 8/1991 | Crivello et al. | 522/172 |
| 5,085,124 A | 2/1992 | Kimura | |
| 5,086,124 A | 2/1992 | Fukuyama et al. | |
| 5,128,431 A | 7/1992 | Riding et al. | |
| 5,512,605 A * | 4/1996 | Eckberg et al. | 522/31 |
| 5,863,970 A | 1/1999 | Ghoshal et al. | |
| 6,084,004 A | 7/2000 | Weinmann et al. | |
| 6,245,828 B1 | 6/2001 | Weinmann et al. | |
| 6,492,433 B1 | 12/2002 | Eckberg | |
| 6,599,960 B1 | 7/2003 | Eckhardt et al. | |
| 6,613,437 B1 | 9/2003 | Eckhardt et al. | |
| 6,693,141 B2 | 2/2004 | Baudin et al. | |
| 6,706,840 B1 | 3/2004 | Williams | |
| 6,779,656 B2 | 8/2004 | Klettke et al. | |

2004/0186202 A1   9/2004   Klettke et al.

FOREIGN PATENT DOCUMENTS

| | | |
|---|---|---|
| DE | 196 48 283 | 5/1998 |
| DE | 197 36 471 | 2/1999 |
| DE | 197 53 461 | 6/1999 |
| EP | 0 306 162 | 3/1989 |
| EP | 0 449 027 | 10/1991 |
| EP | 0 574 265 | 12/1993 |
| JP | 4-180984 A  * | 6/1992 |
| WO | WO 80/02839 | 12/1980 |
| WO | WO 98/22521 | 5/1998 |
| WO | WO 01/51540 | 7/2001 |
| WO | WO 02/066535 | 8/2002 |
| WO | WO 03/085058 | 10/2003 |

OTHER PUBLICATIONS

Abstract fot the article entitled "The Use of Platinum and Rhodium Catalysts for the Preparation and Cationic Ring-Opening Polymerization of Silicon-containing Epoxides" authored by Chung et al. and published in Journal of Polymer Science, Part A: Polymer Chemistry (1993), 31(7), 1741-46.*
Abstract for the article entitled "Novel Platinum Initiators for Ring-Opning Polymerizations" authored by Crivello et al. and published in Makromolekulare Chemie, Macromolecular Symposia (1992) 54/55.*
Crivello et al., "Novel Platinum-Containing Initiators for Ring-Opening Polymerizations," J. Polym. Sci. Part A: Polym. Chem., 1991, 29, 1853-1863.
Crivello et al., "Benzyl Alcohols as Accellerators in the Photoinitiated Cationic Polymerization of Epoxide Monomers," J. Polym. Sci. Part A: Polym. Chem. 2002, 40, 2298-2309.
March, Advanced Organic Chemistry, John Wiley & Sons, New York, 1992, 4th Ed., index, pp. xi, xii, and xiii.
Beringer et al., "Diaryliodonium Salts. IX The Synthesis of Substituted Diphenyliodonium Salts," J. Am. Chem., Soc. 81, 342-351, (1958).
Mason et al., "Organic and Inorganic Chemistry of Iodine Oxides," Nature, 139, 150-151 (1937).
Jenkins et al., "Ligand Transfer of Halides (Cl, Br, I) and Pseudohalides (SCN, $N_3$, CN) from Copper(II) to Alkyl Radicals," J. Org. Chem., vol. 36, No. 21, 3095-3102 (1971).
Jenkins et al., "Kinetics of Ligand Transfer Oxidation of Alkyl Radicals. Evidence for Carbonium Ion Intermediates," J. Org. Chem., vol. 36, No. 21, 3103-3111 (1971).
Jang et al., "Synthesis and Cationic Photopolymerization of Epoxy-Functional Siloxane Monomers and Oligomers," *Journal of Polymer Science Part A: Polymer Chemistry*, Oct. 1, 2003; 41(19):3056-3073.
Jang et al., "Synthesis of Novel Silicon-Containing Monomers for Cationic Photopolymerization," *Polymer Preprints*, 2004; 45(1):587-588.

* cited by examiner

*Primary Examiner*—Marc S. Zimmer
(74) *Attorney, Agent, or Firm*—Sean J. Edman

(57) ABSTRACT

The invention relates to two-component preparations comprising epoxy compounds and a noble metal species, in particular for the preparation of dental compositions. The invention particularly relates to two-component dental compositions which comprise epoxy compounds and are cured by cationic polymerization in the presence of a noble metal species.

24 Claims, No Drawings

CATIONICALLY CURING TWO COMPONENT MATERIALS CONTAINING A NOBLE METAL CATALYST

This application claims priority from EP Application No. 04010330.1, filed Apr. 30, 2004, the entire disclosure of which is herein incorporated by reference.

The invention relates to two-component preparations comprising epoxy compounds and a noble metal species, in particular for the preparation of dental compositions. The invention particularly relates to two-component compositions which comprise epoxy compounds and are cured by cationic polymerization in the presence of a noble metal species and their application in the field of dental materials.

An important parameter of multi-component dental compositions is their processing time. This is understood as meaning the time from the start of setting after mixing of the components to curing of the composition. After mixing the components of the dental composition, the user requires an exactly defined period of time in which he can handle the composition without problems. Directly after this period of time, the composition should harden quickly. A slow solidifying of the composition during processing or working is generally intolerable for the user.

Various systems which attempt to adjust the course of setting of a curing dental composition are known from the prior art.

DE-A-197 53 461 describes, for example, storage-stable cationically polymerizing preparations in which soluble and/or finely divided alkaline earth metal and/or alkali metal compounds allow adjustment of the course of setting. In the case of two-component formulations, the initiator system described there can comprise, inter alia, free Lewis or Bronsted acids. A disadvantage of these preparations is that they allow only a very limited period of time for adjustment of the start of setting, and in addition if the concentration of alkaline earth or alkali metals is increased for the purpose of extending the setting range, they severely delay the end of setting and severely adversely impair the mechanical properties.

Typical examples of reactions which can lead to the acids necessary for initiation of the polymerization of epoxy compounds are redox reactions using bisaryliodonium salts, reducing agents and metal, especially copper complexes, and the dehalogenation of alkyl halides assisted by metal salts. While those reactions often can result in a satisfactory curing behavior, the use of metals, metal complexes or metal salts according to the prior art usually suffers from the fact that the metals, metal complexes or metal salts used according to the prior art generally are either strong coloured or result in strong coloured compounds. Even in low amounts, however, such coloured compounds can disadvantageously alter the appearance of the hardened material. With an increasing patient awareness for aesthetic aspects of dentistry, also the coloration of dental materials is a matter of consideration for the dentist.

Regarding the above-mentioned deficiencies of the prior art, it was an object of the present invention to provide for preparations which are useful as dental materials, which do not exhibit the deficiencies of such materials as they are known from the prior art or at least do not exhibit such deficiencies to an extent as known from the prior art. Especially, it was an object of the present invention to provide for dental materials which allow for a wide range of curing times and allow for a fine tuning of curing times which is highly reproducible. It is also an object of the present invention to provide for compositions which are useful as dental materials which retain the initially desired coloration of the dental material and do not or at least not more than avoidable alter the color of the dental material during curing. It was another object of the present invention to provide for a composition which can be used as a dental material which can reduce the bacterial adhesion to the cured dental material and which can exhibit antimicrobial activity.

The above objects and many other objects which will become apparent to the skilled person from the following description of the present invention are solved by a composition which is useful as a dental material as described in the present text.

The invention thus relates to a preparation comprising at least two components, A and B, wherein at least one of the components, A or B, comprises an epoxy compound and at least one of the components, A or B, comprises a starter which is able to cationically cure the epoxy compound and the component which does not contain the starter contains a noble metal species.

While there is basically an unlimited or at least a high number of components possible in order to specify the preparations according to the invention, e.g., 3, 4, 5, 6 or 7 components, preferably two components, A and B, constitute the preparations according to the present invention.

The epoxy compounds and the Lewis and/or Bronsted acids in the form of compounds which are capable of the formation of Lewis and/or Bronsted acids and do not react with the epoxy compounds can be present in component A or in component B in any desired distribution.

Dental compositions obtained from the preparations according to the invention may comprise, e.g. distributed over two components, A and B, one or more of the following constituents:

a) 10 to 80 wt. %, and preferably 10 to 60 wt. %, of epoxy compounds,
b) 0.01 to 20 wt. %, and preferably 0.1 to 10 wt. %, of compounds which are capable of formation of Lewis or Bronsted acids, and optionally free Lewis and/or Bronsted acids,
c) 10 to 89.99 wt. %, and preferably 30 to 89.99 wt. %, of diluents,
d) 0 to 79.99 wt. %, and preferably 15 to 59.99 wt. %, of modifiers.

Epoxy compounds according to constituent a) can be cycloaliphatic and/or aromatic and/or aliphatic epoxy compounds with at least one epoxy group.

Some cationically polymerizable epoxy resins useful in the compositions of the invention include organic compounds having an oxirane ring, which is polymerizable by ring opening. Such materials, broadly called epoxides, include monomeric epoxy compounds and epoxides of the polymeric type and can be aliphatic, cycloaliphatic, aromatic or heterocyclic. These materials generally have, on average, at least 1 polymerizable epoxy group per molecule, preferably at least about 1.5 and more preferably at least about 2 polymerizable epoxy groups per molecule. The polymeric epoxides include linear polymers having terminal epoxy groups (e.g., a diglycidyl ether of a polyoxyalkylene glycol), polymers having skeletal oxirane units (e.g., polybutadiene polyepoxide), and polymers having pendent epoxy groups (e.g., a glycidyl methacrylate polymer or copolymer). The epoxides may be pure compounds or may be mixtures of compounds containing one, two, or more epoxy groups per molecule.

The "average" number of epoxy groups per molecule can be determined by dividing the total number of epoxy groups in the epoxy-containing material by the total number of epoxy-containing molecules present. These epoxy-containing materials may vary from low molecular weight monomeric materials to high molecular weight polymers and may vary greatly in the nature of their backbone and substituent groups. For example, the backbone may be of any type, and substituent groups thereon can be any group that does not substantially interfere with cationic cure at room temperature. Illustrative examples of permissible substituent groups include halogens, ester groups, ethers, sulfonate groups, siloxane groups, silane groups, nitro groups, phosphate groups, and the like. The molecular weight of the epoxy-containing materials may vary from about 58 to about 100,000 or more.

Some useful epoxy-containing compounds include those which contain cyclohexene oxide groups such as epoxycyclohexanecarboxylates, e.g., typified by 3,4-epoxycyclohexylmethyl-3,4-epoxycyclohexanecarboxylate, 3,4-epoxy-2-methylcyclohexylmethyl-3,4-epoxy-2methylcyclohexane carboxylate, and bis(3,4-epoxy-6-methylcyclohexylmethyl) adipate. For a more detailed list of useful epoxies of this nature, reference is made to the U.S. Pat. No. 3,117,099, which is incorporated herein by reference.

Further examples of epoxy-containing compounds which may be useful in the compositions of this invention include glycidyl ether monomers. Examples are glycidyl ethers of polyhydric phenols obtained by reacting a polyhydric phenol with an excess of chlorohydrin such as epichlorohydrin (e.g., the diglycidyl ether of 2,2-bis-(2,3-epoxypropoxyphenol)-propane). Further examples of epoxides of this type are described in U.S. Pat. No. 3,018,262, which is incorporated herein by reference.

There exist many commercially available epoxy compounds which can be used in this invention. In particular, epoxides which are readily available include octadecylene oxide, epichlorohydrin, styrene oxide, vinyl cyclohexene oxide, glycidol, glycidyl methacrylate, diglycidyl ether of Bisphenol A (e.g., those available under the trade designations "Epon 828", "Epon 825", "Epon 1004" and "Epon 1010" from Shell Chemical Co., "DER-331", "DER-332", and "DER-334", from Dow Chemical Co.), vinylcyclohexene dioxide, 3,4-epoxycyclohexylmethyl-3,4-epoxycyclohexene carboxylate, 3,4-epoxy-6-methylcyclohexylmethyl-3,4-epoxy-6-methylcyclohexene carboxylate, bis(3,4-epoxy-6-methylcyclohexylmethyl)adipate, bis(2, 3epoxycyclopentyl)ether, aliphatic epoxy modified from polypropylene glycol, dipentene dioxide, epoxidized polybutadiene (e.g., "Oxiron 2001" from FMC Corp.), silicone resin containing epoxy functionality, flame retardant epoxy resins (e.g., "DER-580", a brominated bisphenol type epoxy resin available from Dow Chemical Co.), 1,4-butanediol diglycidyl ether of phenolformaldehyde novolak (e.g., "DEN-431" and "DEN-438" from Dow Chemical Co.), and resorcinol diglycidyl ether (e.g., "Kopoxite" from Koppers Company, Inc.), bis(3,4-epoxycyclohexyl)adipate, 2-(3,4-epoxycyclohexyl-5,5-spiro-3,4-epoxy) cyclohexene meta-dioxane, vinylcyclohexene monoxide 1,2-epoxyhexadecane, alkyl glycidyl ethers such as alkyl C-C, glycidyl ether (e.g., "HELOXY Modifier 7" from Shell Chemical Co.), alkyl $C_{12}$-$C_{14}$ glycidyl ether (e.g., "HELOXY Modifier 8" from Shell Chemical Co.), butyl glycidyl ether (e.g., "HELOXY Modifier 61" from Shell Chemical Co.), cresyl glycidyl ether (e.g., "HELOXY Modifier 62" from Shell Chemical Co.), p-ter butylphenyl glycidyl ether (e.g., "HELOXY Modifier 65" from Shell Chemical Co.), polyfunctional glycidyl ethers such as diglycidyl ether of 1,4-butanediol (e.g., "HELOXY Modifier 67" from Shell Chemical Co.), diglycidyl ether of neopentyl glycol (e.g., "HELOXY Modifier 68" from Shell Chemical Co.), diglycidyl ether of cyclohexanedimethanol (e.g., "HELOXY Modifier 107" from Shell Chemical Co.), trimethylol ethane triglycidyl ether (e.g., "HELOXY Modifier 44" from Shell Chemical Co.), trimethylol propane triglycidyl ether (e.g., "HELOXY Modifier 48" from Shell Chemical Co.), polyglycidyl ether of an aliphatic polyol (e.g., "HELOXY Modifier 84" from Shell Chemical Co.), polyglycol diepoxide (e.g., "HELOXY Modifier 32" from Shell Chemical Co.), bisphenol F epoxies, 9,9-bis[4-(2, 3-epoxypropoxy)-phenyl]fluorenone (e.g., "Epon 1079" from Shell Chemical Co.).

Still other epoxy compounds contain copolymers of acrylic acid esters or glycidol such as glycidylacrylate and glycidyl methacrylate with one or more copolymerizable vinyl compounds. Examples of such copolymers are 1:1 styrene glycidylmethacrylate, 1:1 methylmethacrylate glycidylacrylate and a 62.5:24:13.5 methylmethacrylate ethyl acrylate glycidylmethacrylate.

Other useful epoxy compounds are well known and contain such epoxides as epichlorohydrin, alkaline oxides, e.g., propylene oxide, styrene oxide; alchemy oxides, e.g., butadiene oxide; glycidyl esters, e.g., ethyl glaciate. The polymers of the epoxy resin may optionally contain other functionalities that do not substantially interfere with cationic cure at room temperature.

Blends of various epoxy-containing compounds are also contemplated in this invention. Examples of such blends include two or more weight average molecular weight distributions of epoxy-containing compounds, such as low molecular weight (below 200), intermediate molecular weight (about 200 to 10,000) and higher molecular weight (above about 10,000). Alternatively or additionally, the epoxy compound may contain a blend of epoxy-containing compounds having different chemical structures, such as aliphatic and aromatic, or functionalities, such as polar and non-polar. Other cationically polymerizable polymers may additionally be incorporated, if desired.

Especially preferred are cycloaliphatic epoxies like the epoxides described in DE-A-196 48 283, which correspond to the following general formulae:

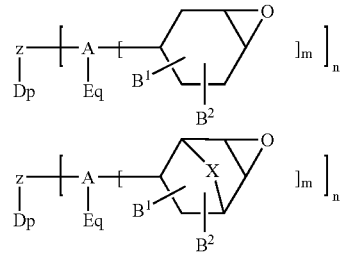

in which the symbols have the following meanings

Z: can be an aliphatic, cycloaliphatic or aromatic radical having 0 to 22, preferably 0 to 18 C atoms, or a combination of these radicals in which one or more C atoms can be replaced by O, C=O, —O(C=O)—, $SiR_2$ and/or NR, wherein R is an aliphatic radical having 1 to 7 C atoms wherein one or more C atoms can be replaced by O, C=O and/or —O(C=O)—, A: can be an aliphatic, cycloaliphatic or aromatic radical having 1 to 18, preferably 1 to 15 C atoms or a combination of these radicals in which one or more C atoms can be replaced by O, C=O, —O(C=O)—, SiR2 and/or NR, wherein R is an aliphatic radical having 1 to 7 C atoms, in which one or more C atoms can be replaced by O, C=O and/or —O(C=O)—, $B^1$, $B^2$, D, E: can be chosen independently of one another, and can be an H atom or an aliphatic radical having 1 to 9, preferably 1 to 7 C atoms in which one or more C atoms can be replaced by O, C=O, —O(C=O)—, $SiR_2$ and/or NR, wherein R can be an aliphatic radical having 1 to 7 C atoms, in which one or more C atoms can be replaced by O, C=O and/or =O(C=O)—, X: can be $CH_2$, S or O, n: can be 2 to 7 or 2 to 5, m: can be 1 to 10, preferably 1 to 7, p: can be 1 to 5, preferably 1 to 4, and q: can be 1 to 5, preferably 1 to 4.

Low-viscosity epoxides such as are described in DE 196 48 283 A can also be employed.

The epoxides known from U.S. Pat. Nos. 2,716,123, 2,985,667, 2,750,395, 2,863,881, 3,187,018, 5,085,124, EP-A-0 449 027 and EP-A-0 574 265 are also very suitable. The latter documents are explicitly mentioned as a source of disclosure for epoxides which can be used according to the teaching of the present invention. The disclosure of the documents U.S. Pat. Nos. 2,716,123, 2,985,667, 2,750,395, 2,863,881, 3,187,018, 5,085,124, EP-A-0 449 027 and EP-A-0 574 265, especially their disclosure with regard to epoxides, is regarded as being part of the disclosure of the present text and is herein incorporated by reference.

In particular, epoxides of the following structural formulae S1 to S12 can be used:

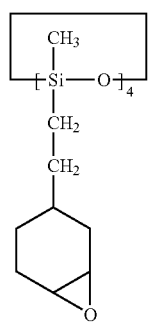

S1

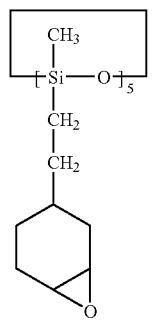

S2

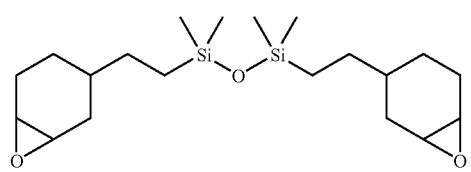

S3

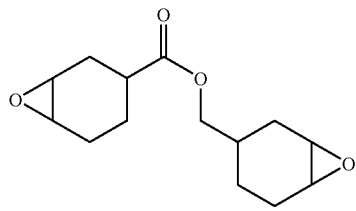

S4

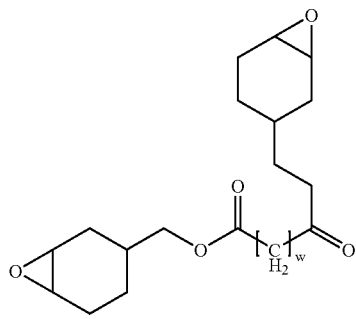

S5 with w=1 to 8, preferably 3 to 5,

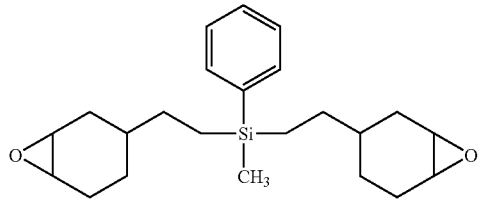

S6

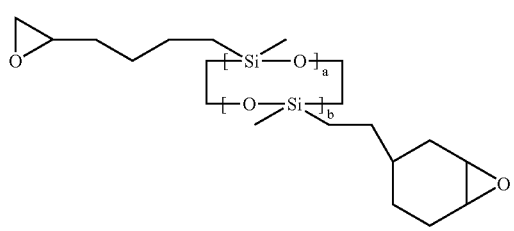

S7

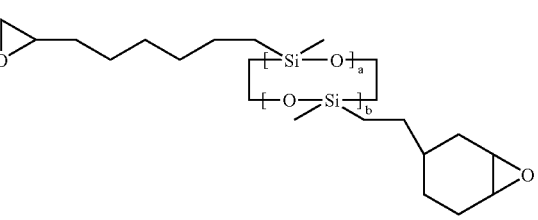

S8

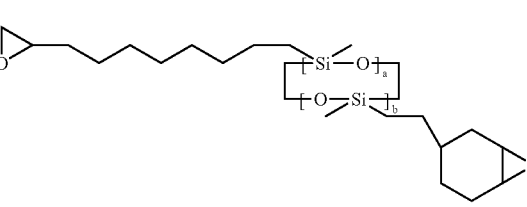

S9 with a=0 to 6, b=0 to 6 and a+b=4 or 5 or 6 and

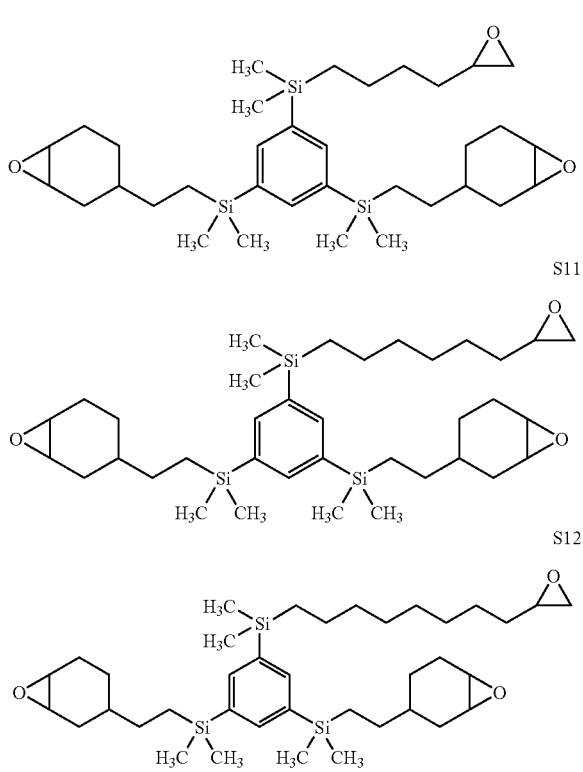

Combinations of aliphatic, cycloaliphatic or aromatic epoxides are possible. Cycloaliphatic epoxy compounds with at least two epoxy groups, cycloaliphatic epoxy compounds with at least four epoxy groups or the combination of cycloaliphatic epoxy compounds with two epoxy groups and cycloaliphatic epoxy compounds with at least four epoxy groups can be advantageous.

Also especially preferred are epoxides as disclosed in U.S. Pat. No. 6,245,828 col. 2, line 17 to col 17, line 28, in WO 02/066535 A1 page 7, line 11 to page 16, line 11 or in WO 01/51540 A2, page 7, line 35 to page 13, line 18. The latter documents are explicitly mentioned as a source of disclosure for epoxides which can be used according to the teaching of the present invention. The epoxides disclosed in the above mentioned documents at the cited locations are regarded as being part of the disclosure of the present text and are herein incorporated by reference. Means to obtain such epoxides are either known to the skilled person or are disclosed in the documents cited above together with examples for obtaining especially preferred epoxides.

It is most preferred to use the following epoxy compounds as a constituent of component A, either alone or as a combination of two or more epoxides: S1, S2, S3, S4, S5, S6, S7, S8, S9, S10, S11 or S12, according to the structural formulae as shown above.

As a constituent of component A or component B, the material according to the present invention contains a starter.

Generally, in the context of the present invention any starter can be used which is able to initiate a cationic polymerization of epoxides as are being used according to the present invention. It is, however, desirable that the starter which is used according to the present invention under ambient conditions does not initiate the cationic polymerization of the epoxides. According to the present invention, e.g., any starter may be used, which, under ambient conditions, is not able to initiate the cationic polymerization of epoxides but which needs a catalyst or an activator in order to form a species which then is able to initiate the cationic polymerization. The term "ambient conditions" means the conditions which the preparation according to the present invention is usually subjected to during storage and handling. Ambient conditions may, for example, be a pressure of about 900 to about 1100 mbar, a temperature of about −10 to about 60° C. and a relative humidity of about 10 to about 100%.

While generally all types of starters which meet the above criteria can be used as starters according to the present invention, it has been found to be advantageous to use Lewis or Bronsted acids as starters. It is known from the prior art that electrophiles $E^+$, i.e., Lewis acidic species, initiate the cationic ring opening polymerization of epoxides. $E^+$ can be $H^+$. H+ can, e.g., be used directly in the form of a strong Bronsted acid like $HBF_4$, $HB(C_6F_5)_4$ $HPF_6$ $HAsF_6$ or $HSbF_6$. If, however, $H^+$ is used directly, the cationic ring opening polymerization is initiated immediately after mixing of $H^+$ and the epoxy resin. To have better control over the polymerization as well as a definite working and setting time (e.g. for the dentist), it is better not to use $H^+$ directly, but to liberate $H^+$ from another species, e.g., by a diffusion controlled process. Thus, in order to have a maximum of control over the polymerization process, it is advantageous to use latent starters. The term "latent starter" is used in the present context to describe starters, which upon contact with the monomer to be polymerized do not initiate the polymerization but start the polymerization upon contact with an agent who transforms the starter into a form which is able to initiate the polymerization.

Since the present invention describes a multi-component system which can contain one starter or a mixture of two or more starters, a starter according to the present invention does not need to be a latent starter as long as it is contained in a component which does not contain an epoxide. Consequently, the preparation according to the present invention can contain different types of starters. If the starter is in the component which contains cationically polymerizable epoxides, it has to be latent starter. If the starter is in the component which does not contain cationically polymerizable epoxides, it can be latent starter but does not have to be. It can be a Lewis acid or a Bronsted acid of the above mentioned type.

In case of latent starter, the Lewis and/or Bronsted acids thus are formed by chemical reactions of selected constituents of the components during or after mixing thereof. Free Lewis and/or Bronsted acids known from conventional systems can also be employed as long as they do not initiate an unwanted polymerization. Where appropriate, to adjust the processing time it is expedient also to employ the substances for delaying cationic polymerization such as those known from DE-A-197 53 461, which reference is expressly mentioned as source of disclosure in the context of the present invention and is herein incorporated by reference. The disclosure of DE-A-197 53 461 with regard to substances for delaying cationic polymerizations is regarded as being part of the disclosure of the present text.

Examples for free acids which may be used as starters according to the present invention are: $BF_3$ or adducts thereof, such as, for example, $BF_3 \exists THF$, $BF_3 \exists Et_2O$, $AlCl_3$, $FeCl_3$, $HPF_6$, $HAsF_6$, $HSbF_6$ and $HBF_4$.

In general, the distribution of the constituents of latent initiation systems between the two components can be undertaken such that premature polymerization of the epoxy compounds during storage of the two-component materials is reliably avoided.

This object can be achieved, for example, by using components which cannot be polymerized by acids and which comprise the critical constituent of the particular latent initiation system, e.g., a halonium salt.

It is known from literature that halonium salts like Hal-$(Ar)_2{}^+ An^-$ can liberate $H^+$ as extremely strong acid $H^+An^-$. It is also known from literature that $H^+$ can be liberated out of, e.g., an iodonium salt in the present of copper ions (see, for example, U.S. Pat. No. 4,342,673, U.S. Pat. No. 4,314, 917, U.S. Pat. No. 4,239,725, WO 80/02839 or U.S. Pat. No. 6,613,437). In these cases copper is used as Cu(I) salt or as a mixture of a Cu(II) salt and a reduction agent like ascorbic acid or fructose to generate a Cu(I) species. Copper is often used in organic chemistry to effect processes in connection with redox transformations as well as silver, mercury, thallium, tin, manganese, samarium, cerium, lanthanum, presodymium, neodymium, cobalt, nickel, zinc or iron. As halonium salts, advantageously iodonium salts are employed.

In the case of the formation of acids by redox reactions from bisaryliodonium salts, reducing agents and copper compounds, as known from the prior art, it has proved expedient to store the bisaryliodonium salts and the reducing agents in a component which comprises no epoxy compounds. A further component then comprises the copper compounds together with the epoxy compounds. This type of separation of the reactive constituents can also be applied in the present invention, e.g., to improve shelf life.

The bisaryliodonium compounds, for example, which are described in U.S. Pat. Nos. 4,225,691 and 4,238,587 are suitable as latent starters according to the present invention. Methods for the preparation of further bisaryliodonium compounds are described in F. M. Beringer, R. A. Falk, M. Karmal, J. Lillien, G. Masullo, M. Mausner, E. Sommers, J. Am. Chem,. Soc. 81, 342 (1958) and I. Mason, Nature, 139, 150 (1937).

Diaryliodonium compounds, which are described, inter alia, in DE A 197 36 471, are particularly preferred. They have the following structure:

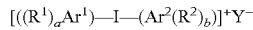

wherein $Ar^1$ and $Ar^2$ can be selected independently of one another and can be different, and are substituted or unsubstituted, fused or non-fused aromatic systems having 4 to 20 C atoms, such as, for example, phenyl, tolyl, cumyl, anisyl, chlorophenyl, nitrophenyl, naphthyl, thienyl, furanyl and pyrazolyl, wherein $R^1$ and $R^2$ can be identical or different and can be independently of one another and can denote an H atom, an aliphatic radical having 1 to 19, preferably 1 to 9 C atoms, and one or more C atoms in an R group can be replaced by O, C=O, —O(C=O)—, F, Cl, Br, $SiR^3{}_3$ and/or $NR_3{}^2$, wherein $R^3$ is an aliphatic radical having 1 to 7 C atoms, in which one or more C atoms can be replaced by O, C=O and/or —O(C=O)—, and a and b can be selected independently of one another and can be 1 to 5. The aromatics $Ar^1$ and $Ar^2$ can be bonded to one another via $R^1$ and/or $R^2$.

The counter-anion $Y^-$ is an anion of low nucleophilicity of the following structure:

wherein K is an element of main group III, V or VII, such as B, Al, P, Sb, As or I, and x can assume numerical values from 1 to 4. The L can be selected independently of one another and can be an aromatic, aliphatic, araliphatic or cycloaliphatic radical having 1 to 25 C atoms, in which one or more C atoms ca be substituted by F, Cl, Br or I, and y can assume numerical values from 0 to 6.

Preferred radicals L are pentafluorophenyl, tetrafluorophenyl, trifluorophenyl, fluorophenyl, phenyl, 4-trifluoromethylphenyl, 3,5-bis(trifluoromethyl)phenyl, 2,4,6-tris (trifluoromethyl)phenyl, fluorine and iodine.

Particularly preferred counter-anions $Y^-$ are $PF_6{}^-$, $AsF_6{}^-$, $SbF_6{}^-$, $B(C_6F_5)_4{}^-$ and $BF_4{}^-$.

Further diaryliodonium compounds are also described, for example, in U.S. Pat. No. 4,246,703, the disclosure of which is herein incorporated by reference.

Particularly suitable diaryliodonium compounds include: diphenyliodonium tetrafluoroborate, diphenyliodonium hexafluorophosphate, diphenyliodonium hexafluoroantimonate, diphenyliodonium tetrakis(pentafluorophenyl(borate)), bis-(4-methylphenyl)iodonium hexafluorophosphate, bis-(4-methylphenyl)iodonium hexafluoroantimonate, bis-(4-methylphenyl)iodonium tetrakis(pentafluorophenyl)borate, phenyl-4-methylphenyliodonium hexafluorophosphate, phenyl-4-methylphenyliodonium hexafluoroantimonate, phenyl-4-methylphenyliodonium tetrakis(pentafluorophenyl)borate, phenyl-4-methoxyphenyliodonium hexafluoroantimonate, phenyl-4-methoxyphenyliodonium tetrakis (pentafluorophenyl)borate, phenyl-3-nitrophenyliodonium hexafluorophenylantimonate, phenyl-3-nitrophenyliodonium tetrakis(pentafluorophenyl)borate, bis(4-tert-butylphenyl)iodonium hexafluoroanitmonate, bis(4-tert-butylphenyl) iodonium tetrakis(pentafluorophenyl)borate, phenyl-4-diphenyliodonium hexafluoroantimonate, dinaphthyliodonium hexafluorophosphate, dinaphthyliodonium hexafluoroantimonate, dinaphthyliodonium tetrakis (pentaflurorphenyl)borate, bis(4-dodecylphenyl)iodonium hexafluoroantimonate, bis(4-dodecylphenyl)iodonium tetrakis(pentafluorophenyl)borate, 4-methylphenyl-4-isopropylphenyliodonium hexafluoroantimonate, 4-methylphenyl-4-isopropylphenyliodonium tetrakis(pentafluorophenyl) borate.

The iodonium salts can be present in the components of the preparation in the amount of 0.01 to 20 wt. %, and preferably 0.2 to 10 wt. %, based on the weight of the mixed material.

Besides at least one epoxy compound and a starter or a mixture of two or more starters, a preparation according to the present invention contains at least one noble metal species as a catalyst. Generally, all noble metal species can be used according to the present invention, which exhibit a sufficient activity towards a catalyzation of the liberation of a starter species from a latent catalyst. Noble metal species which can be employed generally do not exhibit any activity towards the initiation of a cationic polymerization of an epoxide compound. It can be especially preferred to use noble metal compounds, which can be stored together with epoxides, especially with epoxides that can be used in the present invention and do not alter the epoxides in a manner that has a negative influence on the epoxides with regard to their ability to be cured and yield materials which are useful in the context of the present invention. A noble metal species which can be used preferably contains a metal selected from the group consisting of Pt, Pd, Rh, Ir, Os or Ru or a mixture of two or more of these metals. The term "metals", as used in the context of the present invention does not mean clusters of the above atoms bonded by metal-metal-σ-bonds. The term "metal" is intended to identify the above mentioned elements as belonging to the group of metals and does not relate to an actual metallic state of the elements. In fact, in a preferred embodiment, at least one noble metal species present in the preparation does not have detectable metal-metal-σ-bonds. In a further preferred embodiment, none of the noble metal species compounds present in the preparation do have detectable metal-metal-σ-bonds.

It can be further preferred, if the noble metal species is a complex or colloid of a metal selected from the group consisting of Pt, Pd, Rh, Ir, Os or Ru or mixture of two or more of these metals, especially if the complex contains Pt(O) or Pt(II) or Rh(O) or Rh(I)or Pd(O) or Pd(II) or a mixture of two or more of them. It is also preferred, if the noble metal species has at least one olefinic ligand.

It has been found that, despite the large number of known and existing noble metal species, especially compounds with a selected property profile as described below can be very useful and thus may be especially preferred. In a further preferred embodiment, the preparations according to the present invention can contain a noble metal species, which is able to catalyze a hydrosilylation reaction. Surprisingly, the test described below is able to discriminate between components which are useful as noble metal species and components which do not fulfill the task of initiating the starter for a cationic polymerization.

By the term "hydrosilylation" the addition of organosilicon compounds containing silicon-bonded hydrogen to a compound containing an aliphatic multiple bond is meant, and in the test process described in this application, it refers to those processes in which noble metal containing catalysts are tested as to their ability to effect the addition of an organosilicon compound having a silicon-bonded hydrogen atom to an aliphatically unsaturated compound having either olefinic or acetylenic unsaturation.

In order to assess whether a noble metal species was capable of initiating a starter in a preparation according to the present invention, a test system was designed. The resin of the test system for the qualification of a noble metal compound consists of a 1:6 mixture (by weight) of SiH functional siloxanes and poly(ethyleneglycol) diallylether. Within this test system, the noble metal compound (in an amount that is equivalent to 5000 ppm of the noble metal itself with respect to the SiH functional siloxanes and the poly(ethyleneglycol) diallylether together) has to induce an increase of viscosity within, at most, 240 min at room temperature (i.e. 23° C.) under air at normal pressure (i.e. 1023 hPa) in the dark.

As SiH functional siloxanes a 1:1 mixture (by weight) of 1,3,5,7-tetramethyl-cyclotetrasiloxane (D4H) and 1,3,5,7,9-pentamethyl-cyclopentasiloxane (D5H) is used (SiH solution). D4H and D5H are commercially available e.g. from ABCR (A Better Choice for Research Chemicals, Karlsruhe, Germany).

As poly(ethyleneglycol) diallylether poly(ethyleneglycol) (number average molecular weight Mn=600) diallylether (PEG600-diallylether) is used. PEG600-diallylether is commercially available e.g. from Clariant (Clariant Polyglykol AA 600).

As a solvent or dispersion aid for the noble metal compound poly(tetrahydrofuran) (number average molecular weight Mn=250, p-THF 250) is used if the noble metal compound is not soluble in the test system. Poly(tetrahydrofuran) (number average molecular weight Mn=250, p-THF 250) is commercially available e.g. from Sigma-Aldrich.

The qualification of the noble metal compound within this test system is done as follows:

Step 1: At room temperature under air at normal pressure in the dark the noble metal compound is—if neccessary dissolved or dispersed in p-THF 250 (10%-weight of the noble metal compound in p-THF 250)—mixed with PEG600-diallylether.

Step 2: At room temperature under air at normal pressure in the dark the SiH solution is added to this solution or dispersion of the noble metal compound in PEG600-diallylether (and—if neccessary—p-THF 250) and both are mixed by stirring vigorously by hand with a spatula made of polyethylene (PE).

At room temperature under air at ambient pressure in the dark an increase of viscosity occurs within the test system if an increased viscosity is detected by the following method of measurement:

The viscosity is measured with a Bohlin CVO 120 HR device (rotor PP9SS, stator has a diameter of 60 mm, software Bohlin V6.32.1.2). The viscosity is measured at 23.0° C. between two plane and parallel plates (i.e. stator and rotor) which are aligned at a distance of 500 μm with respect to each other. The viscosity is measured as the complex viscosity depending on the oscillation frequency. The oscillation frequency is $1s^{-1}$ with a deformation of 0.01°. The viscosity is given in Pa*s.

At room temperature under air at ambient pressure in the dark an increase of viscosity occurs within the test system if the numerical value of the measured viscosity (in Pa*s) after max. 240 min is higher than the starting numerical value of the measured starting viscosity (in Pa*s) by a factor of at least 3.0.

The following metal compounds did qualify according to the above described test system:

Tris(1,3-divinyl-1,1,3,3-tetramethyl-disiloxan)-diplatin(0) (Karstedt's catalyst): 1 min, a Pt(0) complex prepared from hexachloroplatinum acid by reduction with 1,1,3,3-tetramethyl-1,3-divinylsiloxane in the presence of a vinyl terminated poly(dimethylsiloxane) containing 1.3% by weight of platinum metal as described, e.g., in U.S. Pat. No. 3,715,334, U.S. Pat. No. 3,775,352 and U.S. Pat. No. 3,814,730 for similar platinum complexes: 1 min, Tetrachlor-bis(ethylen)-diplatin(II) (Zeise's salt): 6 min, Dichlor-(norbomadien)-platin(II): 15 min, (1,3,5,7-Tetramethyl-1,3,5,7-tetravinyl-cyclotetrasiloxane)-platin(0) (Ashby's catalyst): 60 min, Tetrakis(triphenylphosphano)-palladium(0): 80 min, Hydrido-carbonyl-tris(triphenylphosphano)-rhodium(I): 80 min, Tetrakis(triphenylphosphano)-platin(0): 105 min, Hexachloroplatinic acid: 115 min.

Thus, according to the present invention any noble metal species can be used, which is able to catalyze the liberation of a starter which, in turn, is able to initiate a cationic polymerization of epoxides being present in the preparation according to the present invention. It can, however, be preferred, if a noble metal species is used, which according to the above described test is able to produce an increase in viscosity in a system according to the above described test within 240 min. or less. In another embodiment of the present invention, a noble metal species can be used, which, according to the above described test, is able to produce an increase in viscosity in the system according to the above described test within 200 min. or less or 150 min. or less or 120 min. or less or 100 min. or less or 80 min. or less or 60 min. or less or 40 min. or less or 30 min. or less or 20 min. or less or 10 min. or less.

In the context of the above described test, an increase in viscosity is detected, when according to the above described viscosity measurement to values, taken at different reaction times, differ such that an increase of viscosity can be detected. It is preferred, if such a difference in viscosity relates at least to a ratio of viscosity of 3.0 or more.

In order to assess the starter initiation capabilities of a qualified noble metal species, an epoxy test system was designed. The resin of the epoxy test system consists of a 1:1 mixture (by weight) of 1,3,5,7-tetrakis[2-(3,4-epoxycyclohexyl)-ethyl]-1,3,5,7-tetramethyl-cyclotetrasiloxane and bis [2-(3,4-epoxycyclohexyl)-ethyl]-methylphenyl-silane (epoxy monomers). These epoxy monomers can be synthesized as described, e.g., in WO 98/22521 (U.S. Pat. No. 6,245,828) and WO 01/51540. The disclosure of WO 98/22521 (U.S. Pat. No. 6,245,828) and WO 01/51540 with regard to the preparation of epoxy monomers is regarded as being part of the disclosure of the present text and is herein incorporated by reference.

As halonium salt (4-cumyl)-(4-tolyl)-iodonium tetrakis (pentafluorophenyl)borate can be used, that is, dissolved in poly(tetrahydrofuran) (number average molecular weight Mn=250, p-THF 250) 1:1 by weight (iodonium salt solution). Within this epoxy test system this iodonium salt (in an amount that is equivalent to 3 %-weight of the iodonium salt itself with respect to the epoxy monomers together) can be used. (4-Cumyl)-(4-tolyl)-iodonium tetrakis(pentafluorophenyl)borate is commercially available e.g. from Rhodia (Rhodia Rhodorsil 2074).

It can further be advantageous with regard to the selection of the noble metal species, when the noble metal species also passes a test according to the epoxy test system as described below.

Within this epoxy test system, the noble metal compound (in an amount that is equivalent to 1000 ppm of the noble metal itself with respect to the epoxy monomers together) has to induce at least an increase of viscosity within max. 16 hours at room temperature (i.e. 23° C.) under air at normal pressure (i.e. 1023 hPa) in the dark. The noble metal compound is used as solution or dispersion in p-THF 250 (10%-weight of the noble metal compound in p-THF 250) (noble metal compound solution).

The test within this epoxy test system is done as follows:

Step 1: At room temperature under air at normal pressure in the dark the epoxy monomers and the iodonium salt solution are mixed (step 1 solution).

Step 2: At room temperature under air at normal pressure in the dark the step 1 solution is added to the noble metal compound solution and both are mixed by stirring vigorously by hand with a spatula made of polyethylene (PE).

At room temperature under air at ambient pressure in the dark, an increase of viscosity occurs within the test system if the numerical value of the measured viscosity (in Pa*s) after max. 16 h is higher than the starting numerical value of the measured starting viscosity (in Pa*s) by a factor of at least 3.0.

The following metal compounds were tested according to the above described epoxy test system:

Tris(1,3-divinyl-1,1,3,3-tetramethyl-disiloxane)-diplatinum (0) (Karstedt's catalyst): 2 min, a Pt(0) complex prepared from hexachloroplatinum acid by reduction with 1,1,3,3-tetramethyl-1,3-divinylsiloxane in the presence of a vinyl terminated poly(dimethylsiloxane) containing 1.3% by weight of platinum metal as described, e.g., in U.S. Pat. No. 3,715,334, U.S. Pat. No. 3,775,352 and U.S. Pat. No. 3,814,730 for similar platinum complexes: 2 min, Bis(ethylene)-tetrachloro-diplatinum(II) (Zeise's salt): 1 h,
(1,5-Cyclooctadien)-dichloro-palladium(II): 1 h,
Dichloro-(norbomadiene)-platinum(II): 1 h 10 min,
Bis(norbomadiene)-dichloro-dirhodium(I): 1 h 10 min,
Hexachloro-platinic acid: 1 h 30 min,
(1,5-Cyclooctadiene)-dichloro-platinum(II): 4 h 20 min,
Bis(triphenylphosphano)-dichloro-palladium(II): 16 h,
(1,3,5,7-Tetramethyl-1,3,5,7-tetravinyl-cyclotetrasiloxane)-platinum(0) (Ashby's catalyst): 16 h.

Besides the above mentioned constituents, a preparation according to the present invention can contain one or more additional components which can modify the properties of the preparation of the present invention either with regard to the single components, especially components A and B before the curing of the preparation, or the material obtained after curing of a preparation according to the present invention.

Diluents as flow improvers can be present in at least one of the components of the preparations according to the invention. Diluents which are usually used as plasticizers can advantageously be employed.

Typical representative materials include the esters of phthalic acid, such as di-2-ethylhexyl phthalate, or the esters of polybasic aliphatic acids, such as dioctyl adipate or acetyl tributylcitrate.

In addition, aliphatic and aromatic hydrocarbons with 6 to 30 C atoms which can be branched or unbranched are very suitable. Typical examples are polypropylene oils or polyisobutylene oils. Advantageously, aromatic hydrocarbons such as polyphenylene compounds, dibenzyltoluene and dibenzylphenyl methane are used.

Polyester polyols which can be prepared, for example, by polycondensation from low-molecular polyols and polycarboxylic acids and/or their anhydrides can also be used.

Typical representatives of this classes are marketed by Huils under the name Dynacoll. Preferably, polyester polyols whose molar masses are between 1000 and 5000 g/mol and hydroxyl equivalent masses of 500 to 2000 are used.

Polyester polyols obtained through catalysed reactions of caprolactone with different starting alcohols are particularly preferred.

Typical representatives of this compound class are marketed by UCC under the name Tone or by Daicel under the name Placcel.

Polycaprolactone triols with molar masses of 200 to 1000 g/mol and polycaprolactone diols with molar masses of 300 to 2000 g/mol can be used.

Furthermore, polycarbonate diols with molar masses of 400 to 2000 g/mol and the general structure

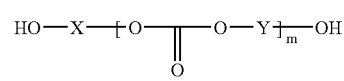

can be used as diluents, X and Y being able to be identical or different and, independently of each other, mean alkylene, arylene, alkarylene, polyoxyalkylene and m can assume values between 1 and 50.

Furthermore, partly epoxidized polybutane diols can optionally be used which represent homopolymerisates of butadiene, which are terminated with OH groups, have molar masses of 1000 to 5000 g/mol and possess a high content of double bonds, which, through epoxidation, can optionally be partly converted to central aliphatic epoxide groups. Representatives of this compound class are marketed by Atochem under the name "Poly bd".

Polyether Polyols of the General Structure

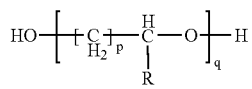

can also be used, q meaning an integer of 20 to 150, p an integer of 1 to 5 and R hydrogen or $C_1$-$C_4$ alkyl.

Preferably, mixed polyether polyols which are composed of propylene oxide units and/or ethylene oxide units and/or tetrahydrofurane units, can be used.

Alkoxy-extended polyols such as for example ethoxylated Bisphenol A or propoxylated trimethylol propane can also advantageously be used.

To adjust the properties, it can be expedient to use mixtures of polyols of different average molar mass and different structure.

Modifiers include, for example, fillers. Fillers can be, for example, quartz, quartz powder, ground or reactive glasses, fragment polymerisates, silica gels as well as pyrogenic silicic acid or their granules, as are customary in the dental field. But other fillers such as, for example, finely-distributed metal or plastic powder, barium sulphate, titanium dioxide or, in general, finely-ground minerals, are suitable. For better incorporation into the polymer matrix, it can be advantageous to hydrophobize the fillers. Hydrophobizing agents are known, and for example, include, silanes such as glycidyloxypropyltrimethoxysilane. The maximum particle size of the inorganic fillers can be 100 µm, and preferably is 20 µm.

As further modifiers, such as dyes or thixotropic agents, or any substances customary in the dental products can be used.

The ratio between the component containing no epoxy compounds and the component containing epoxy compounds can be 1:10 to 1:1, and preferably is 1:5 to 1:2.

The preparations according to the present invention are especially useful for the production of dental materials. The present invention thus also relates to a method for the production of a dental material, wherein at least two components, A and B, are mixed, wherein at least one of components A or B comprises an epoxy compound and at least one of components A or B comprises a starter which is able to cationically cure the epoxy compound, and the component which does not contain the starter contains a noble metal species.

The method according to the present invention makes use of the materials described above. Thus, the details given for the materials above are also part of the description of the method according to the present invention.

Mixing of the separate components of the preparation according to the present invention can be performed in any way known to the person skilled in the art. Mixing can be performed by manual methods, e.g., by mixing with a spatula or the like. Mixing can, however, also be achieved in an automated manner, e.g., by mechanically or electronically driven mechanical devices. Many possibilities are known to the skilled person with regard to automatic mixing devices, especially in the dental field.

The invention is also directed to the use of a noble metal species for initiating a cationic polymerization with a starter, especially if a latent Lewis or Bronstedt acid is used as a starter.

The components of the preparation according to the present invention can be offered and sold separately. It is, however, also possible that the components are offered and sold together as a kit of parts. This may be especially preferable if the kit of parts provides additional value for the user. Such an additional value can, e.g., be storage containers which are adapted for the use in an automated mixing and dosage device or the like.

The two components of the preparations according to the invention can be stored separately, for example in double-chamber cartridges, and be mixed internally before use by eduction via a static or dynamic mixer.

The present invention thus also relates to a kit comprising at least two components, A and B, in separate containers, wherein at least one of components A or B comprises an epoxy compound and at least one of components A or B comprises a starter which is able to cationically cure the epoxy compound, and the component which does not contain the starter contains a noble metal species.

The present invention also relates to a dental material, obtainable from a preparation according to the present invention or by a method according to the present invention.

The present invention also relates to the treatment of a tooth or two or more teeth of a mammal or a human being with a preparation according to the present invention or a dental material obtainable or obtained from a preparation according to the present invention or by a method according to the present invention.

The unique dental materials of the present invention may be filled or unfilled and include dental materials such as direct aesthetic restorative materials (e.g., anterior and posterior restoratives), prostheses, adhesives and primers for oral hard tissues, sealants, veneers, cavity liners, orthodontic bracket adhesives for use with any type of bracket (such as metal, plastic and ceramic), crown and bridge cements, artificial crowns, artificial teeth, dentures, and the like. These dental materials are used in the mouth and are disposed adjacent to natural teeth. The phrase "disposed adjacent to" as used herein will refer to the placing of a dental material in temporary or permanent bonded (e.g., adhesive) or touching (e.g., occlusal or proximal) contact with a natural tooth. The term "composite" as used herein will refer to a filled dental material. The term "restorative" as used herein will refer to a composite which is polymerized after it is disposed adjacent to a tooth. The term "prosthesis" as used herein will refer to a composite which is shaped and polymerized for its final use (e.g., as crown, bridge, veneer, inlay, onlay or the like) before it is disposed adjacent to a tooth. The term "sealant" as used herein will refer to a lightly filled composite or to an unfilled dental material which is cured after it is disposed adjacent to a tooth.

The present invention also relates to the use of a preparation according to the present invention or a dental material obtainable or obtained from a preparation according to the present invention or by a method according to the present invention the treatment of a tooth or two or more teeth of a mammal or a human being.

When the dental compositions are used as model materials in dentistry for the production of working models, many advantages are found: compared with gypsum, the compositions according to the invention show increased mechanical values, such as abrasion resistance, tensile strength and compressive strength. The detail reproduction of fine contours and grooves and the dimensional accuracy, which is largely influenced by the level of polymerization shrinkage, are also considerably better. Compared with model materials of the prior art, which are often based on plastics and are distinguished by cumbersome handling and/or a setting phase larger than gypsum, the dental compositions according to the invention can also be mixed with mechanical mixing aids and the setting phase can be adjusted in an outstanding manner. The end of the setting phase determines the earliest possible point in time at which the model can be removed from the mould and worked further.

In addition to allowing one to tailor curing behavior, the compositions according to the invention also allow for a precise determination of dental material color prior to its curing, undesirable color changes due to the formation of colored by products from the redox materials are avoided.

The preparations are also suitable for other dental applications where low shrinkage is an advantage, for example, as materials for the production of temporary crowns and bridges and fixing cements.

The present invention will be further illustrated by way of the following examples.

EXAMPLES

Gel Times in Comparison to Halonium Salt Based Ternary Redox Systems

Preparation of solution 1

At room temperature in a 100 ml round bottom flask 0.083 g of procetonato-Copper(II) were dissolved in an appropriate amount of ethyl acetate. 9.917 g of bis[2-(3,4-epoxycyclohexyl)-ethyl]-methyl-phenyl-silane were added and after a brief homogenization the solvent was removed under vacuo (0.01 mbar) at 50° C. The amount of procetonato-copper(II) is adjusted so that there are 0.25%-mol of procetonato-copper(II) within the complete resulting mixture of procetonato-copper(II) together with the reducing agent (see below: preparation of Solution 2) and the iodonium salt (see below: preparation of Solution 3).

Preparation of solution 2

As described above for procetonato-copper(II) (see above: preparation of solution 1) as respective reducing agents benzoin (solvent ethyl acetate, Solution 2a) and ascorbyl palmitate (solvent ethanol, Solution 2b) are dissolved within bis[2-(3,4-epoxycyclohexyl)-ethyl]-methyl-phenyl-silane so that there is 1.00%-mol of the reducing agent within the complete resulting mixture of the reducing agent together with procetonato-copper(II) (see above: preparation of solution 1) and the iodonium salt (see below preparation of solution 3).

Preparation of solution 3

As described above for the reducing agents (see above: preparation of solution 2) as respective iodonium salts (4-cumyl)-(4-tolyl)-iodonium tetrakis(pentafluorophenyl) borate (solvent ethyl acetate, solution 3a), (4-ocytyloxy-phenyl)-phenyl-iodonium hexafluorostibonate (solvent ethyl acetate, solution 3b), (4-methoxy-phenyl)-phenyl-iodonium hexafluorostibonate (solvent ethanol, solution 3c), [3-(2-hydroxy-tetradecyloxy)-phenyl]-phenyl-iodonium hexafluorostibonate (solvent ethanol, Solution 3d) and bis (4-tert-butyl-phenyl)-iodonium trifluoromethansulfonate (solvent ethanol, solution 3e) were dissolved in bis[2-(3,4-epoxycyclohexyl)-ethyl]-methyl-phenyl-silane so that there is 1.00%-mol of the iodonium salt within the complete resulting mixture of the iodonium salt together with procetonato-copper(II) (see above: preparation of solution 1) and the reducing agent (see above: preparation of solution 2).

Preparation of Solution 4

As described above for procetonato-copper(II) (see above: preparation of solution 1) but without added solvent, a Pt(0) complex was dissolved in bis[2-(3,4-epoxycyclohexyl)-ethyl]-methyl-phenyl-silane so that the resulting mixture contained 500 ppm of platinum metal of the Pt(0) complex together with the iodonium salt (see above preparation of solution 3). The Pt(0) complex was prepared from hexachloroplatinum acid by reduction with 1,1,3,3-tetramethyl-1,3-divinyldisiloxane in the presence of a vinyl terminated poly(dimethylsiloxane) containing 1.3%-weight of platinum metal as described e.g. within U.S. Pat. Nos. 3,715,334, 3,775,352 and 3,814,730 for similar platinum complexes.

Preparation of the Example Mixtures i. Example Mixtures with a Ternary Initiator System First 1.00 g of Solution 3 was added to 1.00 g of Solution 1. Then 1.00 g of Solution 2 was added. The resulting mixture was then homogenized by vigorously stirring by hand with a spatula made of polyethylene.

ii. Example Mixture with a Binary Initiator System 1.00 g of solution 4 was added to 1.00 g of Solution 3. The resulting mixture was then homogenized by vigorously stirring by hand with a spatula made of polyethylene.

iii. Measurement of the Gel Time

The example mixtures were each hardened at 23° C., 36° C., and 50° C. The gel time was then detected by hand i.e. the time was measured until the resulting mixture had become so hard that the spatula made of polyethylene could no longer be moved within the hardened example mixture. The measurements of the gel time were made after 0.05, 0.10, 0.20, 0.25 h, 0.5 h, 1 h, 2 h, 3 h, and 16 h after preparation of the example mixture. Results are given in Table 1.

iv. Mechanical Properties of Composite Materials Useful as Dental Compositions e.g. as Temporary Crown and Bridge Material The compressive strength and the flexural strength were measured in a way comparable to ISO 9917 and ISO 4049, respectively. For the measurement of the compressive strength, 10 specimens (cylindrical form, diameter 4.00 mm, height 8.00 mm) of each material were prepared according to the manufacturer's recommendations and the measurements were carried out in a way comparable to ISO 9917 using an universal testing machine (Zwick Z 010, crosshead speed 4 mm/min). The compressive strength is given is MPa. For the measurement of the flexural strength 10 specimens (4×6×25 mm) of each material were prepared according to the manufacturers recommendations and the measurements were carried out in a way comparable to ISO 4049 using an universal testing machine (Zwick Z 010, crosshead speed 2 mm/min). The flexural strength is given in MPa. Results are given in Table 2.

TABLE 1

Examples 1 to 8 are comparative examples,
example 9 is an example according to the invention

| Example Mixture | Solutions [g] | | | | | | | | Gel Times [h] | | |
|---|---|---|---|---|---|---|---|---|---|---|---|
| | 1 | 2a | 2b | 3a | 3b | 3c | 3d | 3e | 4 | at 50° C. | at 36° C. | at 23° C. |
| 1 | 1.00 | 1.00 | | 1.00 | | | | | | 1 | 16 | 16 |
| 2 | 1.00 | 1.00 | | | 1.00 | | | | | 1 | 16 | 16 |
| 3 | 1.00 | 1.00 | | | | 1.00 | | | | 16 | 16 | >16 |
| 4 | 1.00 | | 1.00 | 1.00 | | | | | | 0.5 | 0.5 | 2 |
| 5 | 1.00 | | 1.00 | | 1.00 | | | | | 0.5 | 0.5 | 1 |
| 6 | 1.00 | | 1.00 | | | 1.00 | | | | 0.5 | 1 | 16 |
| 7 | 1.00 | | 1.00 | | | | 1.00 | | | 1 | 1 | 16 |
| 8 | 1.00 | | 1.00 | | | | | 1.00 | | 16 | >16 | >16 |
| 9 | | | 1.00 | | | | | | 1.00 | 0.05 | 0.05 | 0.05 |

TABLE 2

| | Examples of Dental Compositions Amounts in %-weight | | |
|---|---|---|---|
| | 1 | 2 | 3 |
| 1,3,5,7-Tetrakis[2-(3,4-epoxycyclohexyl)-ethyl]-1,3,5,7-tetramethyl-cyclotetrasiloxane | 27.9 | 26.4 | 22.1 |
| Bis[2-(3,4-epoxycyclohexyl)-ethyl]-methyl-phenyl-silane | 27.9 | 26.4 | 22.1 |
| p-THF 250 | 6.2 | 9.2 | 14.8 |
| (4-Tolyl)-(4-cumyl)-iodonium Tetrakis(pentafluorophenyl)borate | 2.9 | 2.9 | 5.9 |
| Pt(0) complex I) | 0.1 | 0.1 | 0.1 |
| Silaned Quartz, mean particle size <2 μm | 32.5 | 32.5 | 32.5 |
| Hydrophobized Highly-Disperse Silicic Acid | 2.5 | 2.5 | 2.5 |
| Compressive Strength [MPa] | 203.9 | 221.9 | 174.6 |
| Flexural Strength [MPa] | 83.4 | 80.4 | 67.4 |

I) Platinum(0) complex which was prepared from hexachloroplatinum acid by reduction with tetramethyldivinyldisiloxane in the presence of a vinyl terminated Poly(dimethylsiloxane)

The invention claimed is:

1. A composition comprising at least two components, A and B, wherein at least one of the components, A or B, comprises an epoxy compound and at least one of the components, A or B, comprises a starter that is able to cationically cure the epoxy compound wherein the component that does not comprise the starter comprises a noble metal species comprising a complex or colloid of a metal selected from the group consisting of Pt, Pd, Rh, Ir, Os, Ru or mixture of two or more of these metals.

2. The composition according to claim 1, wherein the starter is a latent starter.

3. The composition according to claim 2, wherein the starter is a latent Lewis or Bronstedt acid.

4. The composition according to claim 1, wherein the starter is an onium salt.

5. The composition according to claim 4, wherein the starter is a halonium salt.

6. The composition according to claim 1, wherein the complex or colloid is essentially free of detectable metal-metal bonds.

7. The composition according to claim 1, wherein the noble metal species is a complex comprising a metal selected from the group consisting of Pt, Pd, Rh or a mixture of two or more such metals, in a low oxidation state, or said noble metal species comprises a mixture of two or more of such complexes.

8. The composition according to claim 7, where in the complex comprises a metal selected from the group consisting of Pt(0), Pt(II), Rh(0), Rh(I), Pd(0), Pd(II) or a mixture of two or more such metals.

9. The composition according to claim 1, wherein the noble metal species has at least one olefinic ligand.

10. A method of making a dental material, comprising mixing at least two components, A and B, wherein at least one of the components, A or B, comprises an epoxy compound and at least one of components, A or B, comprises a starter able to cationically cure the epoxy compound, and wherein the component which does not comprise the starter comprises a noble metal species comprising a complex or colloid of a metal selected from the group consisting of Pt, Pd, Rh, Ir, Os, Ru, or mixture of two or more of these metals.

11. The method according to claim 10, wherein a latent Lewis or Bronstedt acid is used as a starter.

12. A method of initiating a cationic polymerization of an epoxy compound by combining an epoxy compound, a starter, and a noble metal species comprising a complex or colloid of a metal selected from the group consisting of Pt, Pd, Rh, It, Os, Ru or a mixture of two or more of these metals, wherein the stater is an onium salt.

13. A kit comprising at least two components, A and B, in separate containers, wherein at least one of the components, A or B, comprises an epoxy compound and at least one of the components, A or B, comprises a starter able to cationically cure the epoxy compound, wherein the component that does not comprise the starter comprises a noble metal species capable of catalyzing a hydrogenation or hydrosilation reaction.

14. A dental material comprising at least two components, A and B, wherein at least one of the components, A or B, comprises an epoxy compound and at least one of the components, A or B, comprises a starter that is able to cationically cure the epoxy compound wherein the component tat does not comprise the starter comprises a noble metal species capable of catalyzing a hydrogenation or hydrosilation reaction.

15. A dental material obtained by the method comprising mixing at least two components, A and B, wherein at least one of the components, A or B, comprises an epoxy compound and at least one of components, A or B, comprises a starter able to cationically cure the epoxy compound, and wherein the component which does not comprise the starter comprises a noble metal species capable of catalyzing a hydrogenation or hydrosilation reaction.

16. The dental material according to claim 14, wherein the starter is a latent starter.

17. The dental material according to claim 16, wherein the starter is a latent Lewis or Bronstedt acid.

18. The dental material according to claim 14, wherein the starter is an onium salt.

19. The dental material according to claim 18, wherein the starter is a halonium salt.

20. The dental material according to claim 14, wherein the noble metal species is a complex or colloid of a metal selected from the group consisting of Pt, Pd, Rh, Ir, Os, Ru or mixture of two or more of these metals.

21. The dental material according to claim 14, wherein the complex or colloid is essentially free of detectable metal-metal bonds.

22. The dental material according to claim 14, wherein the noble metal species is a complex comprising a metal selected from the group consisting of Pt, Pd, Rh or a mixture of two or more such metals, in a low oxidation state, or said noble metal species comprises a mixture of two or more of such complexes.

23. The dental material according to claim 22, wherein the complex comprises a metal selected from the group consisting of Pt(0), Pt(II), Rh(0), Rh(I), Pd(0), Pd(II) or a mixture of two or more such metals.

24. The dental material according to claim 14, wherein the noble metal species has at least one olefinic ligand.

* * * * *

UNITED STATES PATENT AND TRADEMARK OFFICE
CERTIFICATE OF CORRECTION

PATENT NO.       : 7,368,524 B2
APPLICATION NO.  : 11/109573
DATED            : May 6, 2008
INVENTOR(S)      : Adrian S. Eckert It is certified that error appears in the above-identified patent and that said Letters Patent is hereby corrected as shown below:

On the First Page, in Column 2, under (Other Publications)
Line 1, delete "fot" and insert -- for --, therefor.
Line 7, delete "Opning" and insert -- Opening --, therefor.
Line 13, delete "Accellerators" and insert -- Accelerators --, therefor.

Column 4
Line 57, after "meanings" insert -- : --.

Column 5
Line 1, delete "SiR2" andinsert -- $SiR_2$ --, therefor.

Column 7
Line 42, delete "col" and insert -- col. --, therefor.

Column 8
Line 19, delete "H+" and insert -- $H^+$ --, therefor.
Line 20, delete "$HB(C_6F_5)_4$ $HPF_6$ $HAsF_6$" and insert -- $HB(C_6F_5)_4$, $HPF_6$, $HAsF_6$ --, therefor.

Column 9
Lines 19-20, delete "presodymium," and insert -- praesodymium, --, therefor.
Line 55, delete "$NR_3^2$," and insert -- $NR^3_2$, --, therefor.

Column 10
Line 29, delete "hexafluoroanitmonate," and insert -- hexafluoroantimonate, --, therefor.
Line 34, delete "(pentaflurorphenyl)" and insert -- (pentafluorophenyl) --, therefor.

Column 11
Line 10, delete "Pt(O)" and insert -- Pt(0) --, therefor.
Line 10, delete "Rh(O)" and insert -- Rh(0) --, therefor.
Line 10, delete "Rh(I)or" and insert -- Rh(I) or --, therefor.
Line 10, delete "Pd(O)" and insert -- Pd(0) --, therefor.
Line 67, delete "neccessary" and insert -- necessary --, therefor.

Column 12
Line 7, delete "neccessary" and insert -- necessary --, therefor.
Line 40, delete "(ethylen)" and insert -- (ethylene) --, therefor.
Line 41, delete "(norbomadien)" and insert -- (norbornadiene) --, therefor.

UNITED STATES PATENT AND TRADEMARK OFFICE
CERTIFICATE OF CORRECTION

PATENT NO. : 7,368,524 B2
APPLICATION NO. : 11/109573
DATED : May 6, 2008
INVENTOR(S) : Adrian S. Eckert It is certified that error appears in the above-identified patent and that said Letters Patent is hereby corrected as shown below:

Column 14
Line 3, delete "(norbomadiene)" and insert -- (norbornadiene) --, therefor.
Line 4, delete "(norbomadiene)" and insert -- (norbornadiene) --, therefor.
Line 36, delete "Huils" and insert -- Hüls --, therefor.

Column 15
Line 66, delete "Bronstedt" and insert -- Bronsted --, therefor.

Column 17
Line 66, delete "trifluoromethansulfonate" and insert -- trifluoromethanesulfonate --, therefor.

Column 19
Line 38, after "(dimethylsiloxane)" insert -- . --.
Line 54, in Claim 3, delete "Bronstedt" and insert -- Bronsted --, therefor.

Column 20
Line 19, in Claim 8, delete "where in" and insert -- wherein --, therefor.
Line 26, in Claim 10, after "material" delete ",".
Line 37, in Claim 11, delete "Bronstedt" and insert -- Bronsted --, therefor.
Line 42, in Claim 12, delete "It," and insert -- Ir, --, therefor.
Line 43, in Claim 12, delete "stater" and insert -- starter --, therefor.
Line 57, in Claim 14, delete "tat" and insert -- that --, therefor.

Column 21
Line 4, in Claim 17, delete "Bronstedt" and insert -- Bronsted --, therefor.

Signed and Sealed this

Thirtieth Day of September, 2008

JON W. DUDAS
*Director of the United States Patent and Trademark Office*